US00PP32497P3

(12) United States Plant Patent
Castellarin et al.

(10) Patent No.: US PP32,497 P3
(45) Date of Patent: Nov. 24, 2020

(54) GRAPEVINE PLANT NAMED 'PINOT KORS'

(50) Latin Name: ***Vitis vinifera* L.**
Varietal Denomination: PINOT KORS

(71) Applicants: UNIVERSITÀ DEGLI STUDI DI UDINE, Udine (IT); ISTITUTO DI GENOMICA APPLICATA, Udine (IT)

(72) Inventors: Simone Diego Castellarin, Vancouver (CA); Guido Cipriani, Faedis (IT); Gabriele Di Gaspero, Cividale del Friuli (IT); Michele Morgante, Tricesimo (IT); Enrico Peterlunger, Codroipo (IT); Raffaele Testolin, Udine (IT)

(73) Assignees: UNIVERSITÀ DEGLI STUDI DI UDINE, Udine (IT); ISTITUTO DI GENOMICA APPLICATA, Udine (IT)

( * ) Notice: Subject to any disclaimer, the term of this patent is extended or adjusted under 35 U.S.C. 154(b) by 0 days.

(21) Appl. No.: 16/602,638

(22) Filed: Nov. 12, 2019

(65) Prior Publication Data

US 2020/0205330 P1 Jun. 25, 2020

(30) Foreign Application Priority Data

Dec. 20, 2018 (QZ) ..... PBR 20183518

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ... A01H 5/08; A01H 5/00; A01H 5/02; A01H 5/0812; A01H 6/88
See application file for complete search history.

(56) References Cited

U.S. PATENT DOCUMENTS

PP28,020 P3 * 5/2017 Castellarin ..... Plt./205

* cited by examiner

*Primary Examiner* — June Hwu
(74) *Attorney, Agent, or Firm* — Klarquist Sparkman, LLP

(57) ABSTRACT

A new grape variety distinguished by its strong blistering of the upper side of the leaf blade, cuneiform shaped leaves, fruit cluster of medium bunch density with 3-4 wings, medium harvesting time (early September in northeastern Italy), and resistance to downy mildew and powdery mildew.

4 Drawing Sheets

Latin name of the genus and species of the plant claimed: *Vitis vinifera* L.

Variety denomination: 'PINOT KORS'.

CROSS REFERENCE TO RELATED APPLICATIONS

This application claims the benefit of priority from QZ Community Plant Variety Office (CPVO) Application No. 20183518, filed Dec. 20, 2018.

BACKGROUND

The present application relates to a new and distinct variety of grape named 'PINOT KORS'. The new plant resulted from a controlled cross and is a selection from crossing 99-1-48 (unpatented) as the seed parent with Pinot Noir (unpatented) as the pollen parent in 2007. The resulting plant was selected in 2013 when growing in a cultivated area in Udine, Italy.

'PINOT KORS' is primarily adapted to the climate and growing conditions of the temperate regions with average yearly temperature about 13° C., minimum winter temperature about −20° C., annual rainfall around 700-1500 mm of rain (e.g. North-Eastern Italy, Friuli). This region provides the necessary year-round temperatures required for it to produce and maintain a strong vigorous plant with consistent fruit production.

SUMMARY

The 'PINOT KORS' variety is distinguished from other grape varieties due to the following unique combination of characteristics: strong blistering of upper side of leaf blade, cuneiform shaped leaves, fruit cluster of medium bunch density with 3-4 wings, medium harvesting time (early September in northeastern Italy), and resistance to downy mildew and powdery mildew. A comparison of the new variety to its parents, *Vitis vinifera* 'Pinot Noir' (unpatented) and *Vitis* cross '99-1-48' (unpatented), and to the variety 'MERLOT KANTHUS' (U.S. Plant Pat. No. 28,020) is provided in Table 1.

TABLE 1

| Characteristic | 'PINOT KORS' | 'MERLOT KANTHUS' U.S. Plant Pat. No. 28,020 |
|---|---|---|
| vigour | High | Medium |
| growth habit | Horizontal | Erect |

TABLE 1-continued

| | | |
|---|---|---|
| leaf | Medium, medium green color (upper surface) RHS 134A, strong blistering of upper side of blade, cuneiform shape, small teeth | Small to medium, wedge shaped leaves with medium to medium green (RHS 143B) upper surfaces and light green (RHS 143C) lower surfaces and medium texture |
| cluster | Medium or medium-large conical and loose clusters, with 3-4 wings, berry is medium-to-small of globous shape, blue-black color 99A, thin skin with medium pruinosity, soft pulp with neutral flavor | Low weight, conical with two middle size wings, loose of medium dense, berry skin with blue black color RHS 99A, soft RHS flesh, neutral taste, no flesh coloration |
| harvesting time | Medium early September (Middle Friuli, northeastern Italy) | First decade of September (Middle Friuli, northeastern Italy) |
| resistances | Resistant to downy mildew, resistant to powdery mildew | Resistant to downy mildew, tolerant to powdery mildew |

| Characteristic | Female Parent '99-1-48' | Male Parent 'Pinot noir' unpatented |
|---|---|---|
| vigour | Medium-High | Medium |
| growth habit | Horizontal | Horizontal |
| leaf | Medium, weak blistering of upper side of blade, circular shape, medium teeth | Medium, dark green color (upper surface) RHS N134A, medium blistering of upper side of blade, pentagonal shape, small-medium teeth |
| cluster | | Low weight, with one or two wings, compact, broad ellipsoid berry, berry skin with blue-black color RHS 99A, soft flesh, neutral taste, no flesh coloration |
| harvesting time | Medium early September (Middle Friuli, northeastern Italy) | Early end of August (Middle Friuli, northeastern Italy) |
| resistances | Resistant to downy mildew, resistant to powdery mildew | No resistance to downy mildew, no resistance to powdery mildew |

Of the many commercial cultivars known to the present inventor, the most similar to the new grapevine 'PINOT KORS' is the male parent 'Pinot Noir', to which a comparison has been provided above.

Asexual reproduction of this new variety by grafting onto K5BB rootstock was first performed in February 2014 in Rauscedo, Friuli Venezia Giulia Region, Italy, and has demonstrated that that the foregoing characteristics for the new cultivar come true to form, are firmly fixed, and are established and transmitted through succeeding propagations. The new cultivar reproduces true to type.

Certain characteristics of this variety may change with changing environmental conditions (such as photoperiod, temperature, moisture, soil conditions, nutrient availability, or other factors). Color descriptions and other terminology are used in accordance with their ordinary dictionary descriptions, unless the context clearly indicates otherwise. Color designations (hue/value/chroma) are made with reference to The Royal Horticultural Society (R.H.S.) Colour Chart, $5^{th}$ edition, London, England, 2007.

Figure 1:
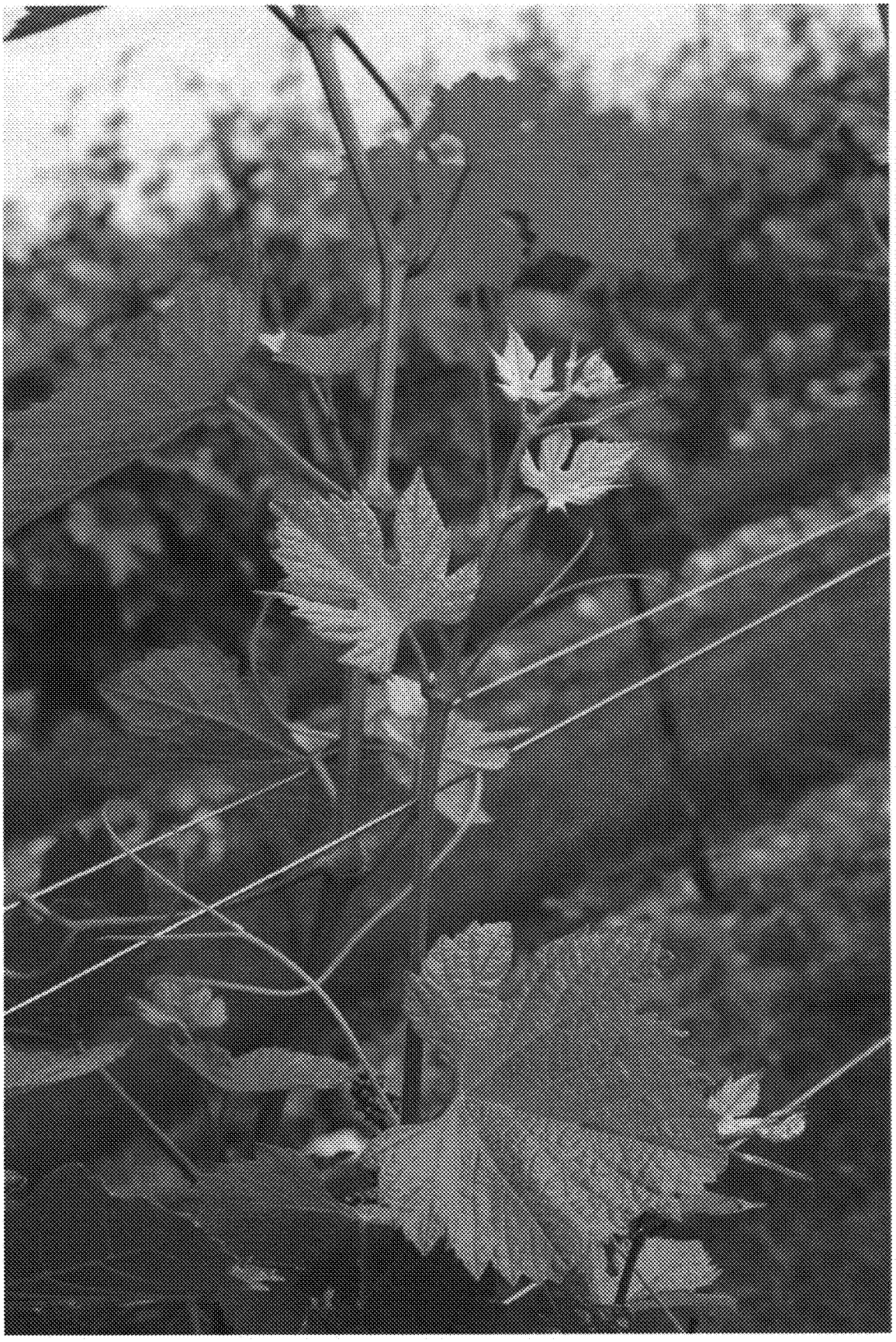
FIG. 1 is a photograph showing a shoot of the new variety 'PINOT KORS' taken on May 24, 2017, in Rauscedo, Italy.
Figure 2:
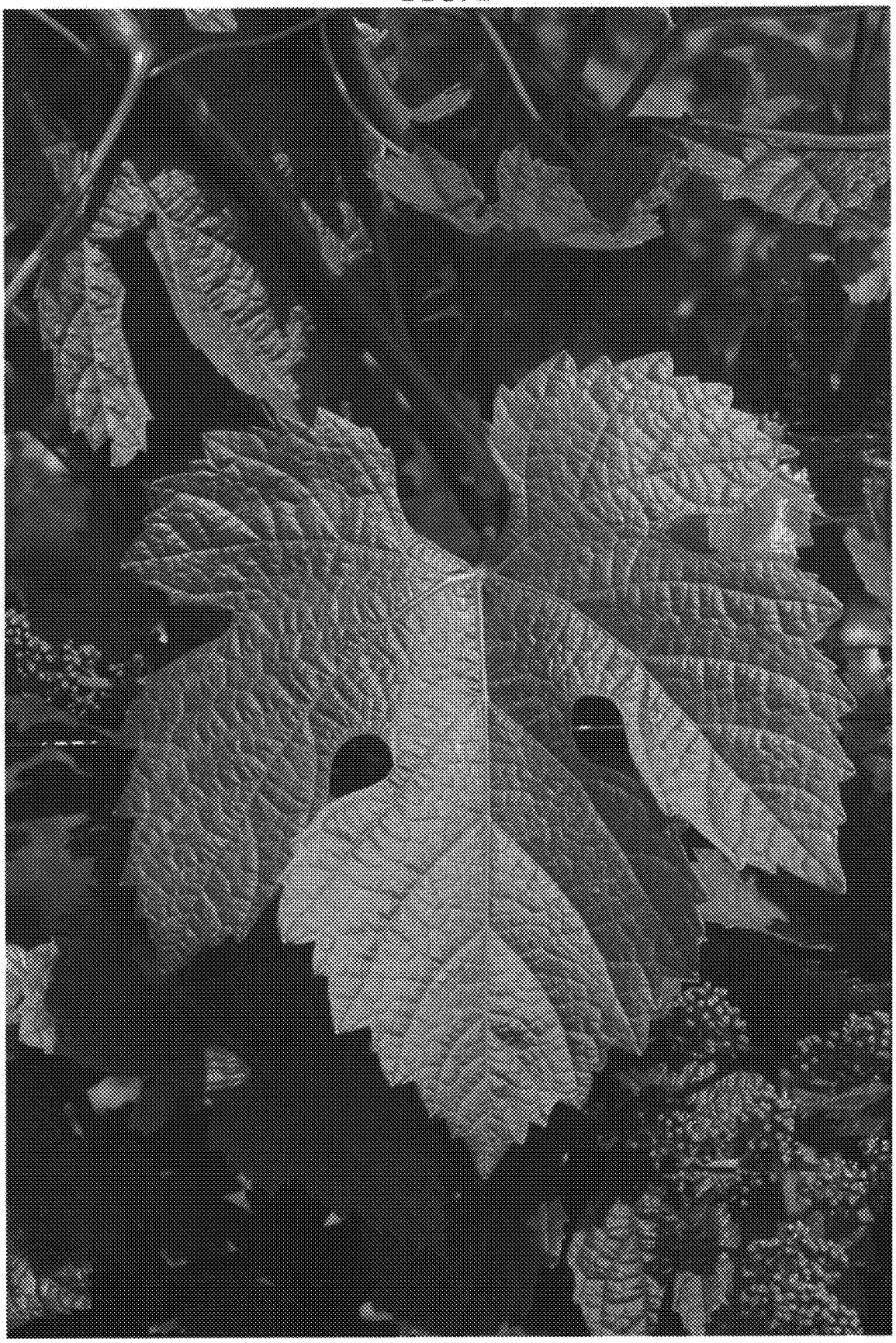
FIG. 2 is a photograph showing a leaf of the new variety 'PINOT KORS' taken on May 24, 2017, in Rauscedo, Italy.
Figure 3:
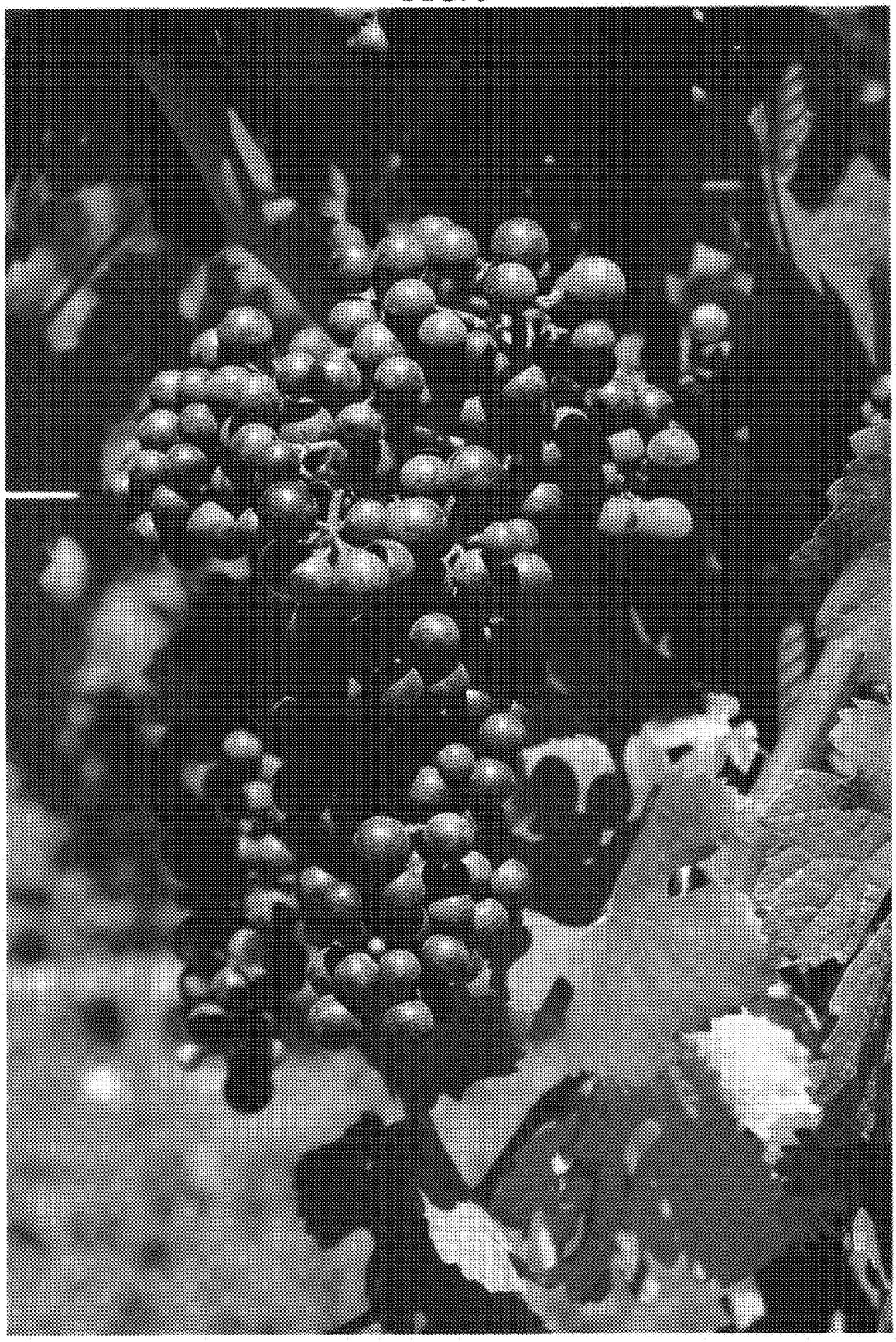
FIG. 3 is a photograph showing fruit of the new variety 'PINOT KORS' taken on Aug. 24, 2016, in Rauscedo, Italy.
Figure 4:
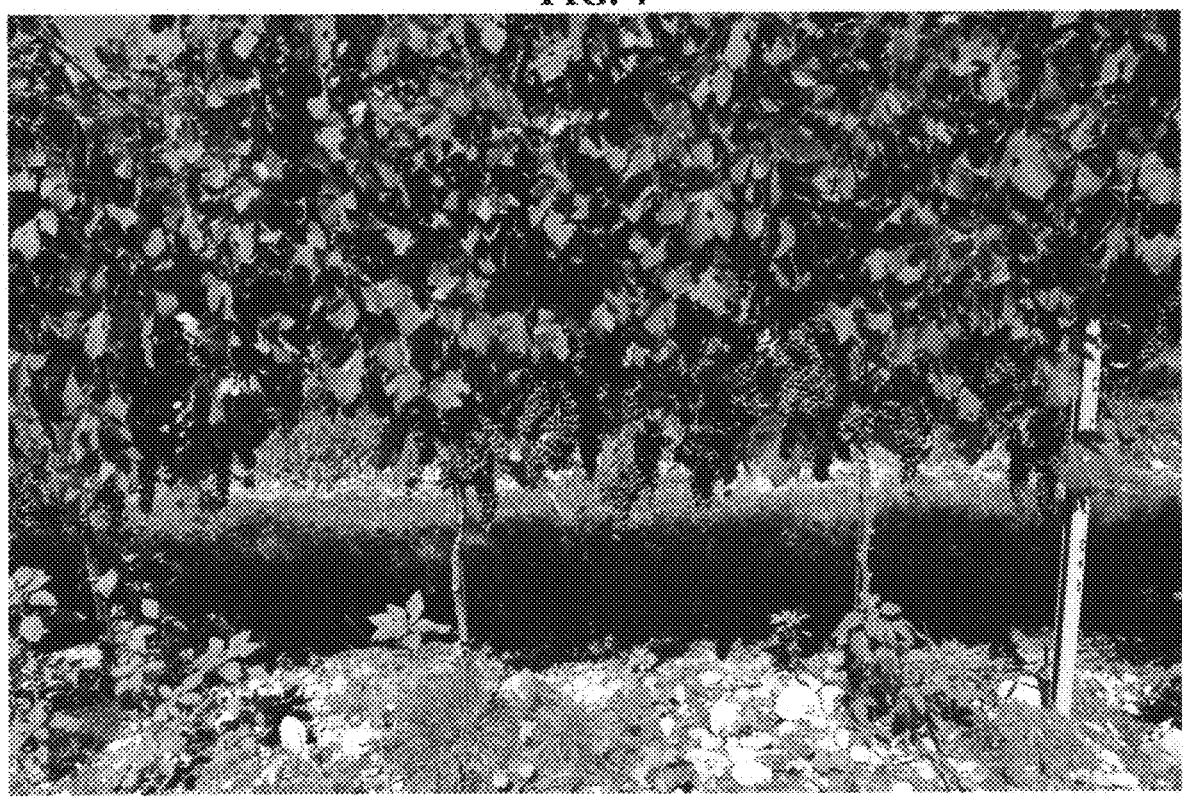
FIG. 4 is a photograph showing plants of the new variety 'PINOT KORS' taken on Aug. 24, 2016, in Rauscedo, Italy.

The color photographs shows typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

The new variety was identified due to its resistance to downy mildew and powdery mildew, and was suited to the climatic and soil conditions of central-northern Italy. The new variety can be used in wine production.

BOTANICAL

The following detailed description of the 'PINOT KORS' variety is based on observations of asexually reproduced progeny. The observed progeny are plants which were 3-5 years of age. The following detailed description concerns the plants growing in an open field taken in Rauscedo, Italy in 2016-2018. The original plant and progeny have been observed growing in a cultivated area in Rauscedo, Italy, with medium texture soil that is rich in skeleton and alluvial in nature. Temperatures in Rauscedo, Italy range from a high of 29° C. to a low of −2° C. Average rainfall is 822 mm per year, with an average rainfall during the growing season (April-September) of 453 mm.

The chart used in the identification of colors described herein is The R.H.S. Colour Chart, 5$^{th}$ edition, except where general color terms of ordinary significance are used. The color values were determined in August-September 2018 under natural light conditions in Rauscedo, Italy.

Scientific name: *Vitis vinifera* L.

Parentage:

*Seed parent.*—99-1-48.

*Pollen parent.*—'Pinot Noir'.

Plant:

*Vigor.*—High.

*Growth habit.*—Horizontal.

Trunk:

*Diameter at 50 cm.*—28 mm (6 yr-old plants).

*Bark texture.*—Striate.

*Bark coloration.*—RHS N187A.

Mature cane:

*Diameter.*—9.6 mm.

*Bark texture.*—Ribbed.

*Bark coloration.*—RHS 179C.

Shoot:

*Opening of the shoot tip.*—Fully open for young shoot.

*Distribution of the anthocyanin coloration of the prostrate hairs of the shoot tip.*—Absent.

*Density of prostate hair on the shoot tip.*—Medium.

*Attitude (before tying).*—Semi-erect to horizontal.

*Color of the dorsal side of internodes.*—Green 140B and red 53D.

*Color of the ventral side of internodes.*—Green 140B and red 53D.

*Distribution of anthocyanin coloration on the bud scales.*—Absent.

*Number of consecutive tendrils.*—2 or less.

Tendrils:

*Length.*—26.5 cm.

*Diameter.*—2 mm.

*Color.*—RHS 145C and 179C.

Leaves:

*Shape.*—Cuneiform.

*Ratio length/width of teeth.*—Small (Marsanne).

*Blistering.*—Strong blistering of upper side of blade.

*Arrangement of lobes of upper lateral sinuses.*—Slightly overlapped (Cabernet Sauvignon).

*Size of blade.*—Medium (Cabernet Sauvignon); average length 132 mm; average width 174 mm.

*Young leaf.*—Color of upper surface is green 134B, color of the lower surface RHS 142C, with sparse prostrate hairs between main veins on the lower side of blade.

*Mature leaf.*—Color of upper surface is medium green 134A, color of the lower surface RHS 140B, with sparse prostrate hairs between main veins on the lower side of blade.

*Mature leaf.*—Five lobes.

*Area of anthocyanin coloration of main veins on upper side and lower of mature blade.*—Only at the petiolar point.

*Goffering/depressions of mature blade between the main veins.*—Absent or very weak (Gamay).

*Undulation of blade between main or lateral veins of mature leaf.*—Absent.

*Profile of mature blade in cross-section.*—V-shaped.

*Degree of opening of petiole sinus.*—Open.

*Shape of base of petiole sinus.*—Brace-shaped ({).

*Petiole sinus base limited by vein.*—On one side.

*Petiole length compared to length of middle vein.*—Slightly shorter (Gloire de Montpellier).

*Petiole average length.*—127 mm.

*Petiole color (upper surface).*—RHS 145B and RHS 179 C.

*Petiole color (lower surface).*—RHS 145B and RHS 184 D.

*Density of prostrate hairs on petiole.*—None or very low.

*Density of erect hairs on petiole.*—None or very low.

*Depth of upper lateral sinuses.*—Deep, average depth of the sinus 53.2 mm.

Flower bud:

*Shape.*—Round.

*Size.*—Average.

*Color.*—Light brown.

*Bud burst.*—Beginning of April in Rauscedo, Italy.

Flowers: Fully developed stamens and fully developed gynoecium.

*Insertion of 1$^{st}$ inflorescence.*—3$^{rd}$ and 4$^{th}$ node.

*Number of inflorescences per shoot.*—1 to 2.

*Flowering period (time of beginning of flowering).*—Beginning of June in Rauscedo, Italy.

*Average flower diameter.*—2 mm.

*Inflorescence average length.*—169 mm.

*Inflorescence average width.*—126 mm.

Fruit:

*Cluster.*—Medium or medium-large conical and loose clusters with 3-4 wings.

*Time of beginning of berry ripening.*—Early to medium.

*Average size of cluster wings.*—Length 65-75 mm; width 50-60 mm.

*Berry shape.*—Globose.

*Berry size.*—Medium to small (length about 13 mm; width about 13 mm).

*Pruinosity.*—Medium.

*Pulp.*—Soft.

*Color of skin (without bloom).*—Blue black 99A.

*Flesh color.*—RHS 150C.

*Skin.*—Thin.

*Anthocyanin coloration of flesh.*—Absent or very weak.

*Flavor.*—None/neutral.

*Berry shipping quality.*—N.a.

*Berry storage quality.*—N.a.

*Formation of seeds.*—Complete.

*Average number of seeds.*—2-3.

*Seed size.*—Medium (Pinot noir, Merlot).

*Seed color.*—Brown RHS 200C.

*Harvest time.*—Medium (early September in northeastern Italy).

*Bunch length (peduncle excluded).*—Long, about 200 mm (Trebbiano toscano).

*Bunch width.*—Medium-wide, about 120-160 mm (Garnacha tinta; Monastrell).

*Bunch density.*—Medium.

*Length of peduncle of primary bunch.*—Medium (about 70 mm; Barbera).

*Color of peduncle.*—RHS 156A and RHS N200A.

*Diameter of peduncle.*—5-7 mm.

*Lignification of peduncle.*—Up to about the middle.
*Berry hilium.*—Visible.

Pedicel:
*Average length.*—7-9 mm.
*Average diameter.*—1-1.5 mm.
*Color.*—RHS 145B.

Grape juice characteristics:
*Sugars* (brix).—22.6.
*Ph.*—3.5.
*Total acidity.*—5.9 g/l.
*Tartaric acid.*—7.3 g/l.
*Malic acid.*—3.99 g/l.

Production characteristics:
*Clusters per shoot.*—1.72.
*Grape production.*—3633 g/plant.
*No. of bunches/vine* (*at harvest*).—22.2.
*Average weight of the bunch.*—276 g.
*Average berry weight.*—1.42 g.
*Pruning wood weight.*—690 g/plant.
*Index of Ravaz.*—5.26.

Wine produced from grapes:
*Total acidity.*—5.4 g/l.
*Tartaric acid.*—1.7 g/l.
*Ph.*—3.7.
*Net extract.*—26 g/l.
*Flavonoids.*—1427 mg/l.
*Anthocyanins.*—330 mg/l.
*Total polyphenols.*—1450 mg/l.
*Alcohol.*—13.9 g/l.
*Volatile acidity.*—0.7 g/l.
*Reducing sugars.*—1.6 g/l.

TABLE 2

| Molecular Analysis | | | | | |
|---|---|---|---|---|---|
| VVS2 | | VVMD5 | | VVMD7 | |
| N + 28 | N + 28 | N + 4 | N + 6 | N + 12 | N + 22 |
| VVMD25 | | VVMD27 | | VVMD28 | |
| N + 14 | N + 14 | N + 8 | N + 14 | N + 2 | N + 28 |
| VVMD32 | | VRZAG62 | | VRZAG79 | |
| N + 5 | N + 5 | N + 14 | N + 26 | N + 8 | N + 16 |

Use international coding based on "N" (see European project GENRES 081—A basis for the preservation and utilization of *Vitis* genetic resources).

Phenological characteristics (in Rauscedo, Italy):
*Germination.*—April 4.
*Flowering.*—June 4.
*Veraison* (*change of color*).—August 3.
*Maturation.*—September 15.

Use: Wine grape.

Disease/pest resistance: Resistance to downy mildew and powdery mildew.

We claim:

1. A new and distinct variety of *Vitis vinifera* L. plant substantially as illustrated and described herein.

* * * * *